United States Patent
Kyogaku et al.

(10) Patent No.: US 9,312,116 B2
(45) Date of Patent: Apr. 12, 2016

(54) MASS DISTRIBUTION SPECTROMETRY METHOD AND MASS DISTRIBUTION SPECTROMETER

(71) Applicant: CANON KABUSHIKI KAISHA, Tokyo (JP)

(72) Inventors: Masafumi Kyogaku, Yokohama (JP); Kota Iwasaki, Atsugi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/343,245

(22) PCT Filed: Oct. 25, 2012

(86) PCT No.: PCT/JP2012/078263
§ 371 (c)(1),
(2) Date: Mar. 6, 2014

(87) PCT Pub. No.: WO2013/073373
PCT Pub. Date: May 23, 2013

(65) Prior Publication Data
US 2014/0224979 A1   Aug. 14, 2014

(30) Foreign Application Priority Data

Nov. 17, 2011  (JP) ................. 2011-251552

(51) Int. Cl.
*H01J 49/14*  (2006.01)
*H01J 49/06*  (2006.01)
(Continued)

(52) U.S. Cl.
CPC .......... *H01J 49/14* (2013.01); *G01N 23/2258* (2013.01); *H01J 49/0004* (2013.01); *H01J 49/0031* (2013.01); *H01J 49/06* (2013.01); *H01J 49/142* (2013.01); *H01J 49/40* (2013.01)

(58) Field of Classification Search
CPC ....... H01J 49/14; H01J 49/142; H01J 49/004; H01J 49/0031; H01J 49/06; H01J 49/40; G01N 23/2258

USPC ........................... 250/282, 288, 287
See application file for complete search history.

(56) References Cited

U.S. PATENT DOCUMENTS 3,480,774 A * 11/1969 Smith .................. G01N 23/203
                                                     250/294
3,567,927 A *  3/1971 Barrington ............ H01J 49/142
                                                     250/282

(Continued)

FOREIGN PATENT DOCUMENTS

EP      0 425 204 A2   5/1991
EP      0 427 532 A2   5/1991
(Continued)

OTHER PUBLICATIONS

"Spread." Merriam-Webster.com. Accessed Sep. 17, 2014. http://www.merriam-webster.com/dictionary/spread.*
(Continued)

*Primary Examiner* — Wyatt Stoffa
(74) *Attorney, Agent, or Firm* — Fitzpatrick, Cella, Harper & Scinto (57) ABSTRACT

The present invention provides a mass distribution spectrometry which reduces an influence of the dispersion in the times at which ionizing beams irradiate a sample, on a mass spectrometry result, and can measure the mass distribution with high reliability. The mass distribution spectrometry is a mass spectrometry which includes irradiating the sample with a primary ion beam and detecting generated secondary ions, wherein this primary ion beam has a spread toward a direction perpendicular to a travelling direction, has a path length of each primary ion contained in the primary ion beam between a primary ion source and a surface of the sample adjusted by deflecting a trajectory, and is obliquely incident on the surface of the sample.

17 Claims, 5 Drawing Sheets

(51) Int. Cl.
  *H01J 49/40* (2006.01)
  *G01N 23/225* (2006.01)
  *H01J 49/00* (2006.01)

(56) References Cited

U.S. PATENT DOCUMENTS

| | | | | |
|---|---|---|---|---|
| 4,058,724 A | * | 11/1977 | McKinney | G01N 23/203 250/292 |
| 4,100,409 A | * | 7/1978 | Brongersma | H01J 49/282 250/305 |
| 4,866,272 A | * | 9/1989 | Aoki | G01N 23/203 250/305 |
| 4,896,035 A | * | 1/1990 | Mahoney | B01D 59/44 313/542 |
| 4,983,831 A | * | 1/1991 | Migeon | H01J 49/40 250/287 |
| 5,026,988 A | * | 6/1991 | Mendenhall | G21K 1/10 250/281 |
| 5,077,470 A | * | 12/1991 | Cody | H01J 49/022 250/282 |
| 5,087,815 A | * | 2/1992 | Schultz | H01J 49/48 250/287 |
| 5,128,543 A | * | 7/1992 | Reed | H01J 37/256 250/287 |
| 5,164,594 A | * | 11/1992 | Thompson | H01J 37/252 250/288 |
| 5,633,495 A | * | 5/1997 | Niehuis | H01J 49/40 250/287 |
| 5,654,544 A | * | 8/1997 | Dresch | H01J 49/025 250/283 |
| 5,665,967 A | * | 9/1997 | Coxon | H01J 49/484 250/287 |
| 5,847,385 A | * | 12/1998 | Dresch | H01J 49/025 250/283 |
| 6,002,128 A | * | 12/1999 | Hill | H01J 37/256 250/281 |
| 6,078,045 A | * | 6/2000 | Maul | G01N 23/2258 250/281 |
| 6,107,629 A | * | 8/2000 | Benninghoven | G01B 15/00 250/398 |
| 8,637,808 B2 | | 1/2014 | Kyogaku et al. | |
| 2003/0193023 A1 | * | 10/2003 | Marsh | G01N 23/2258 250/309 |
| 2006/0163473 A1 | * | 7/2006 | Vestal | H01J 49/06 250/291 |
| 2007/0023678 A1 | * | 2/2007 | Hiraoka | C22C 1/023 250/288 |
| 2007/0187584 A1 | * | 8/2007 | Funsten | H01J 49/40 250/287 |
| 2008/0277576 A1 | * | 11/2008 | Komatsu | H01J 49/142 250/287 |
| 2009/0261243 A1 | * | 10/2009 | Bamberger | H01J 49/0004 250/287 |
| 2009/0272890 A1 | * | 11/2009 | Ogawa | H01J 49/061 250/281 |
| 2010/0227308 A1 | * | 9/2010 | Hashimoto | G01N 33/6848 435/4 |
| 2010/0237242 A1 | * | 9/2010 | Schwarzer | G01N 23/207 250/309 |
| 2011/0069862 A1 | * | 3/2011 | Krizek | H01J 49/0004 382/100 |
| 2011/0248156 A1 | * | 10/2011 | Komatsu | H01J 49/0463 250/251 |
| 2011/0266438 A1 | * | 11/2011 | Harada | H01J 49/0004 250/288 |
| 2012/0025068 A1 | | 2/2012 | Clench et al. | |
| 2012/0301043 A1 | * | 11/2012 | Suga | G06T 5/003 382/254 |
| 2013/0092831 A1 | * | 4/2013 | Kyogaku | H01J 49/00 250/282 |
| 2013/0270432 A1 | * | 10/2013 | Iwasaki | H01J 49/022 250/282 |
| 2014/0110244 A1 | | 4/2014 | Iwasaki | |
| 2015/0115149 A1 | * | 4/2015 | Aoki | H01J 49/0004 250/282 |

FOREIGN PATENT DOCUMENTS

| | | | |
|---|---|---|---|
| JP | 4-94050 A | | 3/1992 |
| JP | 2002-203510 A | | 7/2002 |
| JP | 2006-139996 A | | 6/2006 |
| JP | 2007-157353 A | | 6/2007 |
| JP | 2007157353 A | * | 6/2007 |
| JP | 2008-21504 A | | 1/2008 |
| JP | 2011-522366 A | | 7/2011 |
| WO | 2013/054937 A1 | | 4/2013 |

OTHER PUBLICATIONS

Bruno W. Schueler, "Microscope Imaging by Time-of-Flight Secondary Ion Mass Spectrometry," 3(2-3) Microsc. Microanal. Microstruct. 119-139 (Apr./Jun. 1992) (XP002559196).

E. Niehuis et al., "Design and Performance of a Reflectron Based Time-of-Flight Secondary Ion Mass Spectrometer with Electrodynamic Primary Ion Mass Separation," 5(4) J. Vac. Sci. Technol. A 1243-1246 (Jul. 1987) (XP055206425).

Extended European Search Report in European Application No. 12849986.0 (dated Sep. 22, 2015).

Notification of Reasons for Refusal in Japanese Application No. 2011-251552 (dated Jul. 9, 2015).

\* cited by examiner

MASS DISTRIBUTION SPECTROMETRY METHOD AND MASS DISTRIBUTION SPECTROMETER

TECHNICAL FIELD

The present invention relates to a method of ionizing a substance on a sample, analyzing the substance by mass spectrometry, imaging an in-plane distribution of the substance and outputting the image, and a spectrometer to be used for the method.

BACKGROUND ART

As an analysis method of exhaustively visualizing the distribution information of a large number of substances constituting a living body tissue, an imaging mass spectrometry method which is an application of mass spectrometry method has been progressively developed. In the mass spectrometry method, a sample is ionized by irradiation with laser light or a primary ion, the ionized sample is separated based on the mass-to-charge ratio, and thus a spectrum formed of the mass-to-charge ratio and the detection intensity is obtained. By two-dimensionally analyzing the surface of the sample by mass spectrometry, a two-dimensional distribution of the detection intensities of the substance corresponding to each of the mass-to-charge ratios can be provided, so as to obtain distribution information (mass imaging) of each substance.

As a mass spectrometry method, a time-of-flight ion analysis unit is mainly used in which the sample is ionized and the ionized object substance is separated and detected based on a difference between periods of flight time of ions flying from the sample to a detector. As for a unit configured to ionize the sample, there are known a Matrix Assisted Laser Desorption/Ionization method (MALDI) which irradiates a sample that has been mixed in a matrix and crystallized, with laser light that has been pulsed and finely converged, so as to ionize the sample, and a Secondary Ion Mass Spectrometry method (SIMS) which irradiates a sample with a primary ion beam so as to ionize the sample. Among these methods, the imaging mass spectrometry method using MALDI or the like as the ionization method has been already widely used for analysis of a living body sample including protein, lipid and the like. However, in the MALDI method, because of the principle of using a matrix crystal, a spatial resolution is restricted to approximately several tens of µm. On the other hand, a Time-Of-Flight Secondary Ion Mass Spectrometry method (TOF-SIMS) in which an ion irradiation type of ionization method is combined with a time-of-flight ion detection method has a high spatial resolution of a submicron order, and accordingly it has received attention in recent years.

In conventional imaging mass spectrometry methods using these methods, a sample is scanned with an ionization beam, so that a large number of fine measurement regions are sequentially analyzed by mass spectrometry, and thereby the two-dimensional distribution information is obtained. The method has a problem of needing a large amount of periods of time for obtaining a mass image in a wide region.

In order to solve this problem, a two-dimensional detection (projection) type of mass spectrometric method is proposed. In this method, components of a wide region are collectively ionized and these ions are projected onto a detecting device, so as to acquire mass information and two-dimensional distribution of the components in the wide region at one time, which can largely shorten a measurement time. For instance, Japanese Patent Application Laid-Open No. 2007-157353 discloses an imaging mass spectrometer which simultaneously analyzes the components by mass spectrometry and detects the two-dimensionally distributed components by simultaneously recording detection time and detection positions of ions.

In SIMS, whereas the axis of an ion optical system which forms a mass spectrometry section is arranged in a direction perpendicular to the surface of the substrate, in contrast, an ionized beam is usually obliquely incident on the substrate.

Since in the projection type of mass spectrometer a wide region is irradiated at one time with the use of a primary ion beam or the like having a large beam diameter, the nonuniformity of an irradiation density of the primary ion beam significantly gives an influence on the uniformity of an ionization efficiency. As a result, the nonuniformity becomes a cause of significantly degrading the reliability of the mass distribution spectrometry.

In regard to this, in an ion injection apparatus described in Japanese Patent Application Laid-Open No. 2006-139996, a unit is disclosed which is configured to irradiate a substrate having a wide area with ions so that the ion current density becomes equal.

In the projection type of mass spectrometer represented in Japanese Patent Application Laid-Open No. 2007-157353, if a primary ion is used for ionization, there have been the following problems. Specifically, when primary ions which have been pulsed and have a wide spread are obliquely incident on the substrate, the times at which the primary ions reach the substrate is dispersed within the plane. As a result, the times at which secondary ions are generated are also dispersed. When the projection type of mass spectrometer is combined with the time-of-flight (TOF) ion detection method which measures time of flight of the ions and separates the masses from each other, in particular, the mass resolution is degraded by the dispersion in the times at which the secondary ions are generated, and the mass spectrometer results in not being capable of correctly measuring the mass distribution.

When the spectrometer in Japanese Patent Application Laid-Open No. 2006-139996 is applied to a primary ion beam source, the ion irradiation density on the surface of the sample can be uniformized. The spectrometer, however, cannot become an effective unit of solving the dispersion in periods of time during which the pulsed primary ions reach the surface of the sample.

CITATION LIST

Patent Literature

PTL: Japanese Patent Application Laid-Open No. 2007-157353
PTL: Japanese Patent Application Laid-Open No. 2006-139996

SUMMARY OF INVENTION

The method according to the present invention is a mass distribution spectrometry method which includes irradiating a sample with a primary ion beam and detecting a generated secondary ion, wherein this primary ion beam has a spread toward a direction perpendicular to a travelling direction, has a path length of each primary ion contained in the primary ion beam between a primary ion source and a surface of the sample adjusted by deflecting the trajectory, and is obliquely incident on the surface of the sample.

Furthermore, the spectrometer according to the present invention is a mass distribution spectrometer including a primary ion irradiation unit and a detecting device for a secondary ion which has been generated by irradiation for a sample with a primary ion, wherein the primary ion irradiation unit is configured to: form a primary ion beam which has a spread toward a direction perpendicular to a travelling direction; adjust a path length of each primary ion contained in the primary ion beam between a primary ion source and a surface of the sample, by deflecting a trajectory of the primary ion; and irradiate the surface of the sample obliquely with the primary ion of which the path length for each primary ion has been adjusted.

Further features of the present invention will become apparent from the following description of exemplary embodiments with reference to the attached drawings.

DESCRIPTION OF EMBODIMENTS

The present invention can be widely applied to a secondary-ion mass spectrometry method provided with a method for ionizing a sample by irradiating the sample with a primary ion beam and a projection type of ion detection method. The present invention can significantly provide an advantage originating in suppressing the dispersion in the times at which secondary ions are generated on the surface of a sample, by suppressing the dispersion in the times at which primary ions reach the surface of the sample, particularly when a time-of-flight (TOF) ion detection method is adopted. This is because in the TOF ion detection method of measuring time of flight of the ions and separating the masses from each other, the dispersion occurs in the times at which the ions reach a detector even if the ions are the same, due to the dispersion in the times at which the secondary ions are generated, and consequently the dispersion occurs in the detected flight time as well. The dispersion in the detected flight time results in degrading mass resolution, and hinders the correct measurement of mass distribution. When the present invention is applied to the mass spectrometry, the degradation of the mass resolution can be suppressed particularly in the TOF-SIMS, and a mass image of high reliability can be acquired.

Figure 1:
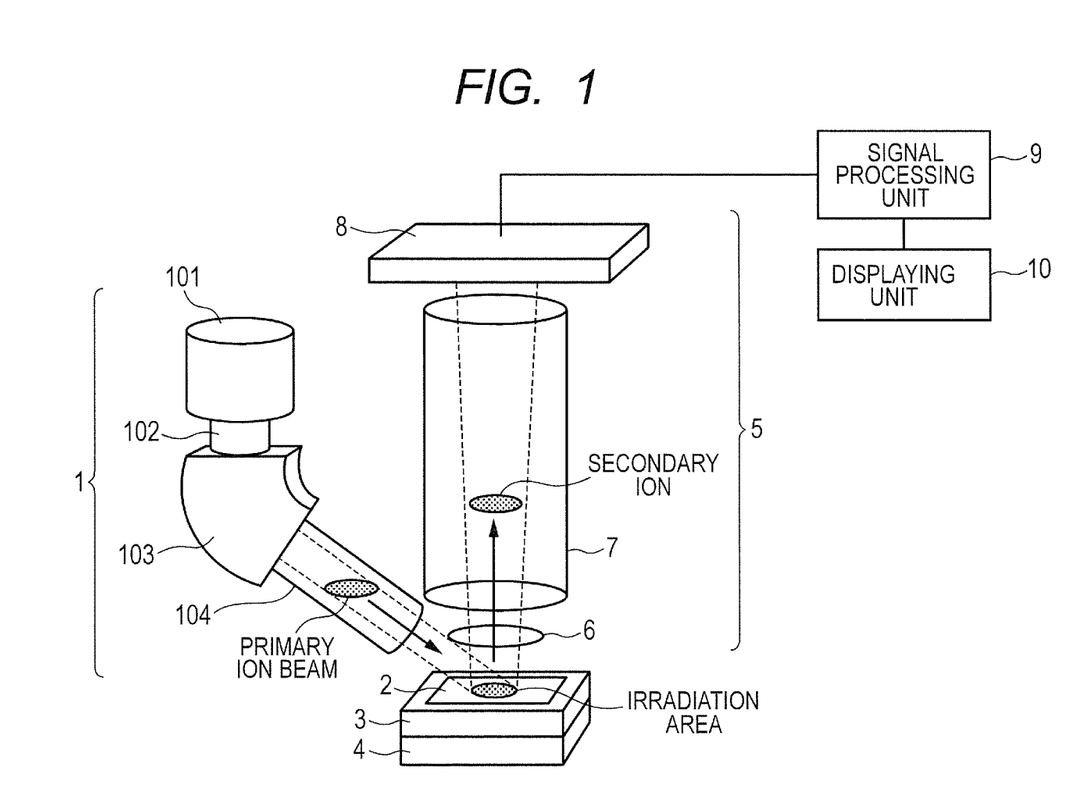
FIG. 1 is a schematic view for illustrating an outline of a structure of a spectrometer according to an embodiment of the present invention.

The mass distribution spectrometry method of the present invention and the structure of the spectrometer to be used in the method of the present invention will be described below with reference to FIG. 1. FIG. 1 is a schematic view for illustrating an outline of a structure of a spectrometer for carrying out a method according to an embodiment of the present invention. While, from the above described viewpoint, the embodiment will be described here while taking a projection TOF type of mass spectrometry as an example, these descriptions merely concern one embodiment of the present invention, and the present invention is not limited thereto.

The spectrometer of the present invention is a mass distribution spectrometer which uses primary ions for ionizing a sample and uses a projection TOF type of ion detecting device. The spectrometer includes: a sample stage 4 for mounting a sample 3 thereon; a primary ion irradiation unit 1 for irradiating the sample 3 with primary ions; a secondary ion detecting unit 5 for detecting secondary ions which have been generated on the surface of the sample; an acquiring unit 9 for acquiring mass distribution on the surface of the sample from signals of the secondary ions which have been detected by the detecting device; and a displaying unit 10 for outputting the acquired mass distribution as an image. The acquiring unit 9 is a signal processing unit for forming the mass distribution on the surface of the sample from the detected signals of the secondary ions, and it includes a control unit such as a computer. The displaying unit is a unit configured to output a result of mass distribution spectrometry, and it includes an image forming unit such as an image display unit and a unit for outputting a data of the mass distribution.

The sample 3 is in a solid form. An organic compound, an inorganic compound or a living body sample can be provided as the sample. The sample 3 is fixed on a substrate 2 having an approximately flat surface. The substrate 2 is mounted on the sample stage 4. The sample stage 4 has a translational mechanism, and by moving the sample stage 4 arbitrarily in an XY direction, it can set an arbitrary region on the sample 3 as a region to be measured.

In a scanning type of TOF-SIMS, the primary ion beam is used generally in a form of being converged to a diameter of approximately 1 µm, or 1 µm or smaller. In contrast to this, a mass distribution spectrometer of the present invention, which is a projection type, uses a primary ion beam that has been planarly spread in a direction perpendicular to a travelling direction, in order to detect two-dimensionally positional information of secondary ions at a time when the secondary ions are generated. In other words, the primary ion beam is an ion group which has a pseudo-discoidal shape or a pseudo-cylindrical shape, and which has a spatial spread. The irradiation area of the primary ion beam on the sample is set according to the size of an area to be measured. When an area containing a plurality of cells in a living body sample is measured, for instance, the size can be set at approximately several tens of µm to several mm.

Usable primary ions include: an ion of a liquid metal such as $Bi^+$ and $Ga^+$; a cluster ion of a metal such as $Bi^+$ and $Au^+$; a cluster ion of a gas such as Ar. The cluster ion is particularly effective for the living body sample because of having an effect of reducing damage against the living body sample.

The primary ion beam is emitted from the primary ion irradiation unit 1 to incident on the sample 3, in a pulsed shape each having an extremely short period of time. In response to this, the secondary ion which has been excited by the primary ion is generated on the surface of the sample. The ionizing beam is incident on the surface of the sample from a direction oblique to the surface of the substrate 2, so as to avoid an interference with an ion optical system constituting the ion detecting device.

The secondary-ion analysis unit 5 includes an extraction electrode 6, a time-of-flight mass spectrometry section 7, and a two-dimensional ion detection section 8. The generated secondary ions pass through the mass spectrometry section 7 while retaining a positional relationship of the ions at positions at which the secondary ions are generated on the surface of the sample 1, and the ions are detected in the two-dimensional ion detection section 8.

The extraction electrode 6 and the substrate 2 are arranged so as to have a space of approximately 1 to 10 mm from each other, and a voltage Vd for extracting the secondary ions is applied to the electrode and the substrate. As the Vd, a positive or negative voltage of 100 V to 10 kV is applied thereto. The secondary ions having a mass m are accelerated by the voltage Vd and incident on the mass spectrometry section. A plurality of electrodes which constitute a projection type of optical system may be appropriately arranged in a rear stage of the extraction electrode 6 (not shown). These electrodes have a zooming function for controlling a spatial spread of the secondary ions, of which magnification can be arbitrarily set by changing voltages applied to the electrodes.

The mass spectrometry section 7 includes a cylindrical mass spectrometry tube which is referred to as a flight tube. The electric potential within the flight tube is constant, so that the secondary ions can fly in the flight tube at a fixed velocity. Since the flight time is proportional to a square root of a mass-to-charge ratio (m/z; m represents a mass of an ion, and z represents electric charge of an ion), the mass-to-charge ratios of the generated secondary ions can be analyzed by measuring the flight time from a difference between a generation time and a detection time of the secondary ions.

The secondary ions which have passed through the mass spectrometry section 7 are projected onto the two-dimensional ion detection section 8. Signals are output on the two-dimensional ion detecting unit 8 so that the detection time and a position on the two-dimensional detecting device of each of the ions are associated. A projection adjustment electrode (not shown) which constitutes an ion lens for adjusting a projection magnification may be arranged between the two-dimensional ion detection section 8 and the mass spectrometry section 7.

Considering the enhancement of the mass resolution, it is advantageous that the length of the flight tube is longer. In the case of the projection type, the elongation of the flight tube facilitates the magnification to be easily increased, and thus a spatial resolution can also be increased. However, the elongation of the flight tube has such a difficult point that the size of the spectrometer becomes large. Therefore, the length of the flight tube can be set in a range of 1,000 mm or longer and 3,000 mm or shorter.

The two-dimensional ion detection section 8 may have any structure as long as the detection section can detect the time and the positional information at which the ions are detected. As the structure of the two-dimensional ion detecting unit 8, for instance, a structure can be used in which a microchannel plate (MCP) and a fluorescent plate or a two-dimensional photodetector such as a charge coupled device (CCD) type are combined with each other. If such a CCD type detector or the like as to be used in an ultrahigh speed camera is used, the periods of time for each image can be divided by a shutter which operates at high speed. Since the CCD type detector can separately image ions which have reach the detector at different times in every imaging frame, an ion distribution image in which the masses have been separated can be acquired at one time.

Figure 2:
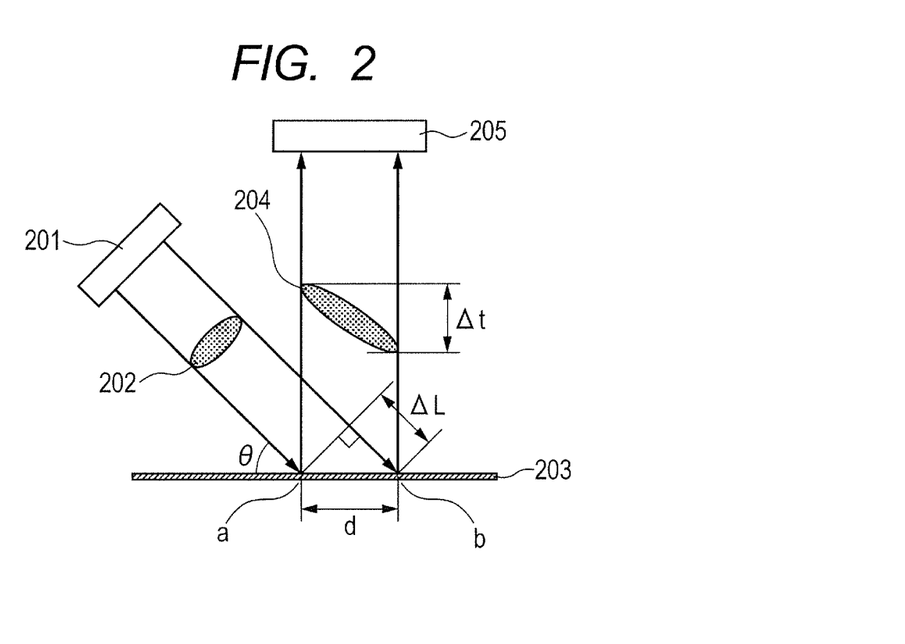
FIG. 2 is a schematic view for describing a difference among the times at which primary ion beams reach the surface of a sample, in a conventional technology.

With reference to FIG. 2, the dispersion in the times at which primary ions reach the sample within the plane on the surface of a sample will be described below, which occurs when a primary ion beam that has been linearly emitted from an ion generation source is obliquely incident on the surface 203 of the sample in a conventional primary ion irradiation unit 201.

Suppose that when primary ions 202, which have been emitted from the primary ion irradiation unit 201, irradiate the flat surface 203 of the sample. On the surface of the sample, a is defined as a measurement point which the ion reaches in the earliest time, b is defined as a measurement point which the ion reaches in the latest time, and d is defined as a distance between a and b. Note that d is not always the maximal value of the distance between two points which the ions reach in an incident direction of the ion beam, and thus, rather, in order to facilitate understandings, it can be defined as a distance between arbitrary two points in the incident direction of the ion beam. In other words, d may be defined as a distance in the incident direction of the ion beam, between arbitrary two points within a range projected when the ion beam which is incident from a oblique direction has been projected onto a horizontal plane on the surface of the sample. Suppose that θ is defined as an angle formed by the surface 203 of the sample and the travelling direction of the ion beam, and in other words, it is defined as an angle formed by the surface 203 of the sample and the incident direction of the primary ions 202 which are incident on either a point a or a point b. From the geometric relationship, in the vicinity on the surface of the sample, a path difference $\Delta L$ of ions which are incident on the point a and the point b is expressed by $\Delta L = d * \cos\theta$. When v is defined as the incident velocity of the ion, a difference $\Delta t$ between the times at which ions incident on the point a and the point b reach the respective points is expressed by $\Delta t = \Delta L/v$.

An influence of the dispersion in the reaching times of the ions on the mass spectrometry result will be described below with reference to FIG. 2. The difference $\Delta t$ between the times at which the primary ions 202 reach the surface 203 of the sample leads to a difference between the times at which the secondary ions 204 are generated. Furthermore, a difference of $\Delta t$ shall be produced in the times at which generated secondary ions 204 that have certain masses m (or m/z; z is a valency of ion) reach a detection surface of the secondary ion detector 205, between the point a and the point b. Consequently, $\Delta t$ is added to the measured value for the period of flight time of the ions, and a difference of up to $\Delta t$ may be produced in the periods of flight time of any ions having the masses m. In other words, "dispersion" of up to $\Delta t$ may be produced in the detection times for the secondary ions, in the measurement points between the point a and the point b.

Suppose that Vacc is defined as the accelerating voltage of the secondary ions, Ltube is defined as the length of the flight tube, e is defined as an elementary electric charge, and t is defined as the flight time, the difference $\Delta t$ of periods of the flight time for certain ions having the masses m corresponds to a difference of the mass, which is $\Delta m = 2ze * Vacc * (\Delta t/Ltube)^2$. In other words, it can be said that an ambiguity of up to $\Delta m$ is produced in the mass separation result. Thereby, there is the possibility that the mass resolution is degraded by several u (u: unified atomic mass unit) or more, depending on the emission condition of the primary ions, the size of the irradiation area of the beam, and the like.

The two-dimensional ion detection section 8 measures the distribution of the secondary ions which have reached the detector for a period of shutter time that has been previously set. Because of this, when there is the dispersion in the reaching times of the secondary ions within the plane, the detection section detects signals concerning a certain secondary ion having a mass m, in which a signal of a part of the certain secondary ions is lost or a signal of an ion having a mass different by $\Delta$m at a maximum is mixed. As a result, there is a possibility that the mass distribution cannot be correctly measured.

In the present invention, the primary ion irradiation unit 1 of the mass distribution spectrometer has a function of deflecting the ion trajectories, and correcting the ion trajectories so that a difference of a path length between the ion source and the surface of the sample becomes smaller. Specifically, as for the above described arbitrary two points on the surface of the sample, the path length are adjusted so that the difference of the path lengths of the ions which are incident on each point becomes smaller than $\Delta L = d*\cos\theta$. By this adjustment function, the primary ions can be adjusted so as to collectively reach the surface of the sample.

Figure 3:
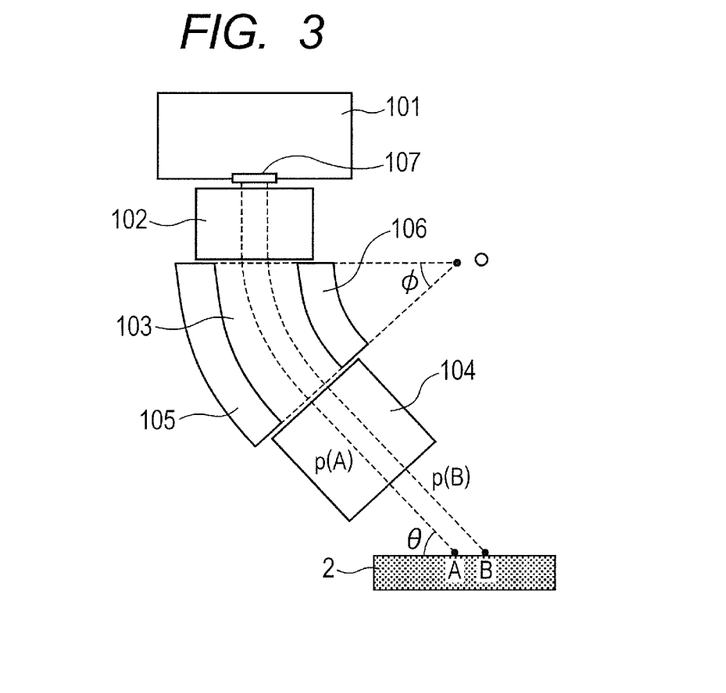
FIG. 3 is a schematic view for describing a primary ion irradiation unit according to an embodiment of the present invention.

With reference to FIG. 3, the primary ion beam irradiation unit 1 according to the present invention includes a primary ion generation section 101, a connection section 102, an ion deflection section 103, and an introduction section 104. The primary ion beams having a spread are emitted in a pulsed shape with a period of time t1 or shorter, from an ion emission aperture 107 of the primary ion generation section 101. The connection section 102 connects the ion generation section 101 with the ion deflection section 103. The primary ions which have been emitted from the ion generation section 101 pass through the connection section 102, and the ions are incident on the ion deflection section 103. The trajectories of the primary ions are changed in the ion deflection section 103, and the resultant primary ions pass through the introduction section 104 to be introduced onto the surface of the sample 2 on the substrate 3. The primary ions are incident on the surface of the substrate 3 obliquely at an angle of $\theta$. Note that, even if the connection section 102 and/or the introduction section 104 have been omitted, the ionizing-beam irradiation unit can have the equivalent function.

The inner parts of the connection section 102 and the introduction section 104 are decompressed or evacuated. In addition, the connection section 102 and the introduction section 104 are surrounded by a conductive member, such that the electric potential of the inner parts thereof is constant, and the ions fly while the velocities are kept. For information, the connection section 102 may have a function of slightly correcting the trajectories of the ions by having facing electrodes arranged therein and applying a weak voltage to the electrodes.

The ion deflection section 103 changes the trajectories of the primary ions and changes the path lengths of each of the primary ions. Suppose that p(A) is defined as a path of an ion which reaches an arbitrary point A on the surface of the sample 2, and that p(B) is defined as a path of an ion which reaches a point B. The ion deflection section 103 adjusts the ion trajectories so that the path lengths of the p(A) and the p(B) become equal. Thereby, when the ions which are emitted from the primary ion generation section 101 have the same velocities, the ions result in reaching the point A and the point B at the same time. Similarly, the trajectories of the ions are adjusted so that the path lengths of all ions become equal. In other words, the ion deflection section 103 works as a deflection unit which deflects the paths of the primary ions toward an incident direction so that the times at which the emitted primary ions reach the surface of the sample become equal.

The ion deflection section 103 includes a first deflection electrode 105 and a second deflection electrode 106 which are a pair of electrodes that oppose to each other so as to sandwich a space for keeping a gap $\Delta$R. The pair of electrodes are sector electrodes positioned to have the gap of which the outer peripheral portion and the inner peripheral portion form arcs having curvature radii R1 and R2 ($\Delta R = R1 - R2$), respectively. Here, suppose that $\phi$ [radian] is defined as a displacement angle in the center O of the arc. In the ion deflection section 103, voltages of Vg1 and Vg2 are applied to the first deflection electrode 105 and the second deflection electrode 106, respectively, and thereby an electric field is generated in the inner part. By applying an electrostatic force which works so as to direct the ions flying in the ion deflection section 103 substantially toward the center O side, all of the ion paths are changed toward one direction, though the amounts of displacement may be different between each path.

The width of the gap through which the ions of the ion deflection section 103, the connection section 102 and the introduction section 104 pass is set at a sufficiently large value with respect to the spread of the trajectories of the primary ions. In addition, the voltages of the Vg1, the Vg2 and the like are adjusted so that the primary ions do not collide with a component member of the primary ion irradiation unit. For information, a correction electrode (not-shown) may be appropriately provided in the vicinity of the inlet and/or the vicinity of the outlet of the ions of the ion deflection section 103. The correction electrode is formed of a pair of electrodes, which can be used for correcting the spread of the electric field and suppressing the disturbance of the ion trajectories.

Suppose that r(A) and r(B) are defined as the curvature radii of the p(A) and the p(B) in the ion deflection section 103, respectively, the path lengths in the ion deflection section 103 are expressed by $r(A)*\phi$ and $r(B)*\phi$, respectively. Therefore, when $\Delta r$ is defined as $r(A)-r(B)$, the difference of path lengths produced between the p(A) and the p(B) in the ion deflection section 103 approximately becomes about $\Delta r*\phi$.

As described above, when the primary ions are obliquely incident on the surface of the sample, the path difference $\Delta L$ in the vicinity of the surface of the sample is expressed by $\Delta L = d*\cos\theta$. Therefore, when each parameter is adjusted so that $\Delta r*\phi$ approximately equals $d*\cos\theta$, the path lengths of the ion trajectories of the p(A) and the p(B) can be equalized to each other. Note that, since the curvature radius of the ion trajectory is changed by the change of a direction in the ion deflection section, in the strict sense, each parameter is determined by an ion optical simulation. The ion deflection section 103 can have a function of changing the angle $\phi$ or a voltage applied to the deflection electrode, according to the change of the incident angle $\theta$ of the primary ions or the irradiation range of the primary ions, with reference to the above described result. The ion deflection section 103 can also have a function of changing the curvature radii of the electrodes 105 and 106, respectively.

Here, a unit configured to deflect the ion trajectory toward one direction by the ion deflection section formed of a pair of deflection electrodes has been described. Otherwise, the path lengths of the ion trajectories can be equalized as a whole by the combination of a plurality of ion deflection sections.

Further, although a method of deflecting the ion trajectory with an electrostatic force has been used herein for the ion deflection section, a method of deflecting the ion trajectory with a magnetic force may otherwise be used. If so, a unit is provided which is configured to apply a static magnetic field, for instance, perpendicularly to a direction in which the ions are deflected. However, in the method using the magnetic field, there is a problem that the method needs a strong magnetic field in order to deflect the trajectories of heavy ions, and the size of the spectrometer results in being large. There is also a problem that the magnetism having leaked from a magnetic field applying unit deforms the trajectory of the ion in the mass spectrometry section, which may give a bad influence on a mass spectrometry result. In consideration of the above problems, the ion deflection section can adopt a method of using the electrostatic force.

As described above, the above described ion irradiation unit 1 suppresses the dispersion in the times at which the ions reach the surface of the sample, which is caused by the difference of the path lengths of individual primary ions. Note that the present invention does not reduce the dispersion corresponding to the pulse width t1, which occurs at the time when the primary ions have been emitted from the primary ion generation section.

Thus, the present embodiment can suppress the dispersion in the times at which the primary ions reach the surface of the sample, even when the primary ion beam having a spread has obliquely irradiated the surface of the sample. Furthermore, the present embodiment can acquire a mass image of high reliability, in which the degradation of the mass resolution has been more suppressed than in a conventional method, particularly when the TOF type of the ion detecting unit is adopted, by suppressing the dispersion in the times at which the secondary ions are generated on the surface of the sample.

Exemplary Embodiment 1

A first exemplary embodiment according to the present invention will be described below with reference to FIG. 4A and FIG. 4B which illustrate a part of a primary ion irradiation unit and a simulation result of an ion trajectory.

Figure 4A:
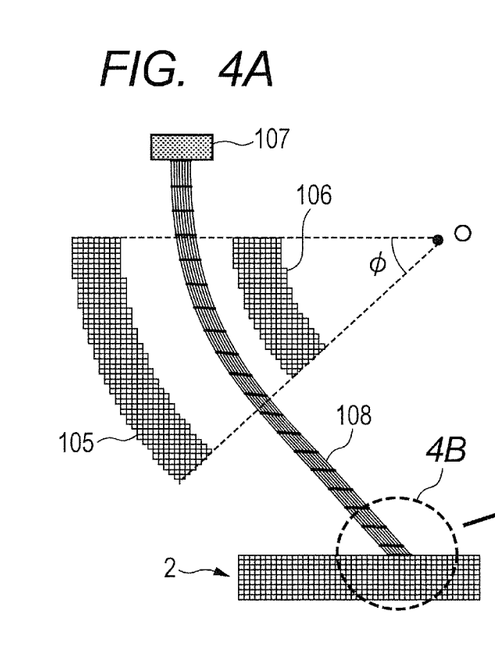
FIG. 4A is a schematic view for illustrating a structure of a primary ion irradiation unit and an outline of a calculation result of an ion trajectory, according to a first exemplary embodiment of the present invention.

FIG. 4A illustrates the arrangement of an ion emission window 107, a first deflection electrode 105 and a second deflection electrode 106 which constitute an ion deflection section 103, and a sample 2. The descriptions are omitted in regard to a primary ion generation section 101, a connection section 102 and an introduction section 104.

In FIG. 4A, the ion trajectories of primary ions which have been emitted from the ion emission window 107 are represented by a curve 108. The primary ions are emitted at the same time from the ion emission window 107. Points on the curve 108 represent the positions of each ion at the time when a fixed period of time has passed after the primary ions had been emitted from the ion emission window 107 of the primary ion generation section 101. FIG. 4B is an enlarged view in the vicinity of a portion in which a sample 2 is irradiated with the primary ion beam, in FIG. 4A.

In the present exemplary embodiment, the energy of the ions which are emitted from the primary ion generation section was set at 6 keV. In the ion deflection section, R1 was set at 60 mm, R2 was set at 40 mm, ΔR was set at 20 mm, and φ was set at 45 [deg]. The potential Vs on the surface of the sample 2 was set at 0V. The voltages of Vg1 and Vg2 applied to the first deflection electrode 105 and the second deflection electrode 106 were set at 1,250 V and −2,500 V, respectively. In addition, the incident angle θ of the beam on the surface of the sample was set at 50 [deg]. A spread d of the beam when the beam was incident on the surface was set at approximately 4 mm.

Figure 4B:
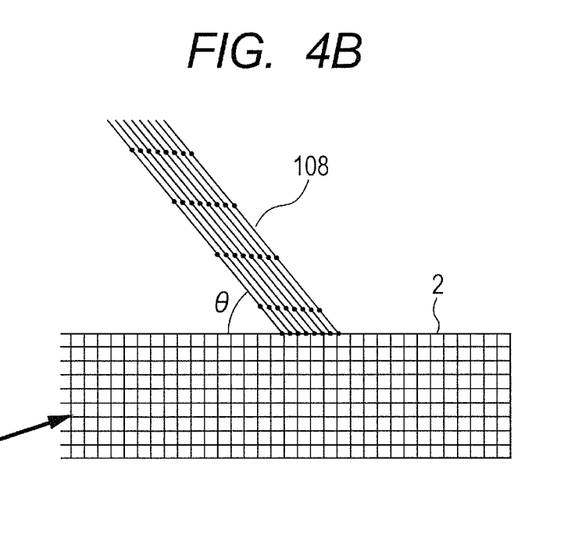
FIG. 4B is an enlarged view of the calculation result of the ion trajectory in the vicinity of the surface of a sample, according to the first exemplary embodiment of the present invention.

As is illustrated in FIG. 4B, each of the primary ions reaches the surface of the sample 2 almost at the same time. Specifically, the dispersion in the path lengths of the primary ions was 0.35 mm at a maximum. In the case of a Bi ion, the emission velocity of the primary ions on the emission surface is approximately 75 km/sec, and consequently the times at which the primary ions reach the surface of the sample are converged into 5 nsec or shorter.

As described above, the structure in the present exemplary embodiment can suppress the dispersion in the times at which the primary ions reach the surface of the sample, even when the primary ion beam having a spread has obliquely irradiated the surface of the sample. The structure also enables the primary ion source to be provided in the vicinity of a secondary ion detecting device, and it enables the size of the spectrometer to be decreased.

Exemplary Embodiment 2

Figure 5A:
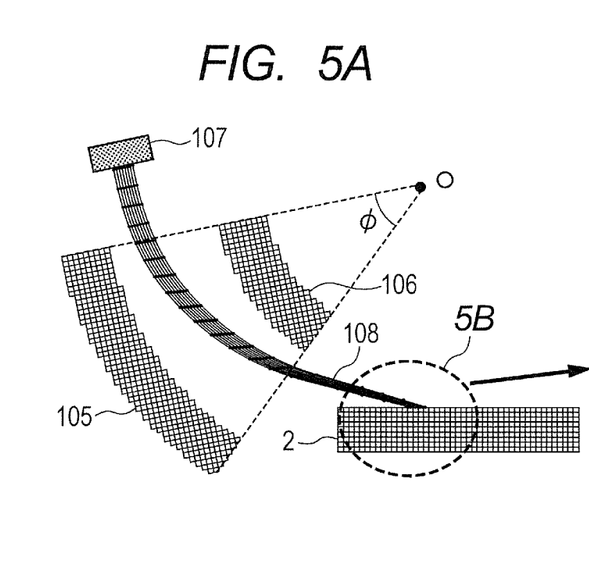
FIG. 5A is a schematic view for illustrating a structure of a primary ion irradiation unit and an outline of a calculation result of an ion trajectory, according to a second exemplary embodiment of the present invention.
Figure 5B:
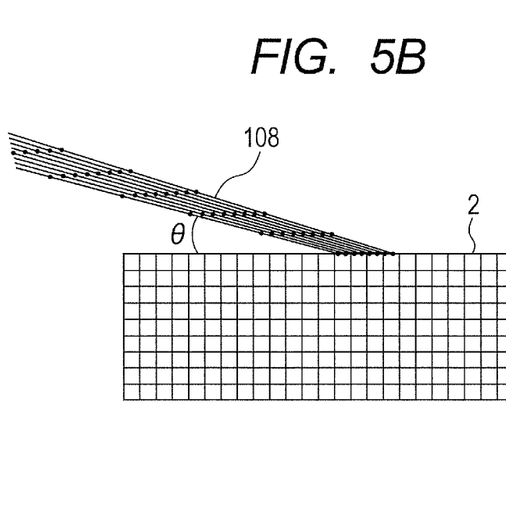
FIG. 5B is an enlarged view of the calculation result of the ion trajectory in the vicinity of the surface of a sample, according to the second exemplary embodiment of the present invention.

A second exemplary embodiment according to the present invention will be described below with reference to FIG. 5A and FIG. 5B which illustrate a part of a primary ion irradiation unit and a simulation result of an ion trajectory. FIG. 5B is an enlarged view in the vicinity of a portion in which a sample 2 is irradiated with the primary ion beam, in FIG. 5A.

The present exemplary embodiment is different from Exemplary Embodiment 1 in the arrangement of the ion irradiation unit 1 and the sample 2, the setting of the parameters and the beam trajectory. The structures which are common with those of the above described Exemplary Embodiment 1 are denoted by the same reference numerals, and the descriptions are omitted.

In the present exemplary embodiment, energy of the ion emitted from the primary ion generation section was set at 4 keV. In the ion deflection section, R1 was set at 60 mm, R2 was set at 40 mm, ΔR was set at 20 mm, and φ was set at 45 [deg]. The potential Vs of the surface of the sample was set at 0 V. The voltages of Vg1 and Vg2 applied to the electrodes of the ion deflection section were set at 1,250 V and −2,500 V, respectively. In addition, the incident angle θ of the beam on the surface of the sample was set at approximately 16 [deg]. A spread d of the beam when the beam was incident on the surface was set at approximately 2.6 mm.

In the present exemplary embodiment, paths of the primary ions are converged, and the spread of the beam on the surface of the sample is reduced by 25% compared to the spread in an ion window. However, as is understood also from FIG. 5b, each primary ion reaches the surface of the sample almost at the same time. Specifically, the dispersion in the path lengths of the primary ions was 0.35 mm at a maximum. Consequently, in the case of a Bi ion, the times at which the primary ions reach the surface of the sample are converged into 5 nsec or shorter.

For information, if parameters such as the applied voltage have been adjusted, it is also possible to expand the beam trajectory and to make the primary ions reach the surface of the sample at the same time.

As described above, the present exemplary embodiment also can suppress the dispersion in the times at which the primary ions reach the surface of the sample, when the primary ion beam having a spread has obliquely irradiated the surface of the sample. In addition, in the present exemplary embodiment the ions can be converged and consequently the ion density can be increased.

Exemplary Embodiment 3

Figure 6A:
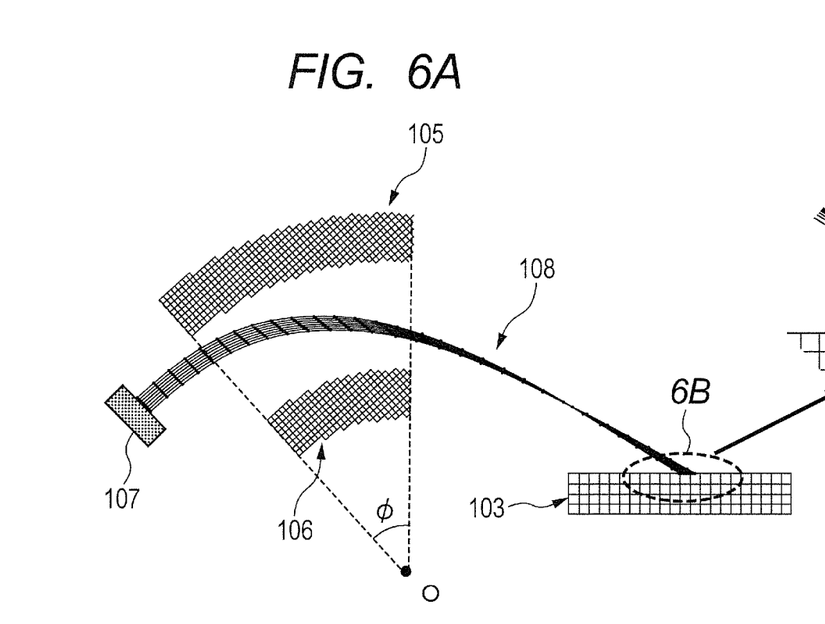
FIG. 6A is a schematic view for illustrating a structure of a primary ion irradiation unit and an outline of a calculation result of an ion trajectory, according to a third exemplary embodiment of the present invention.
Figure 6B:
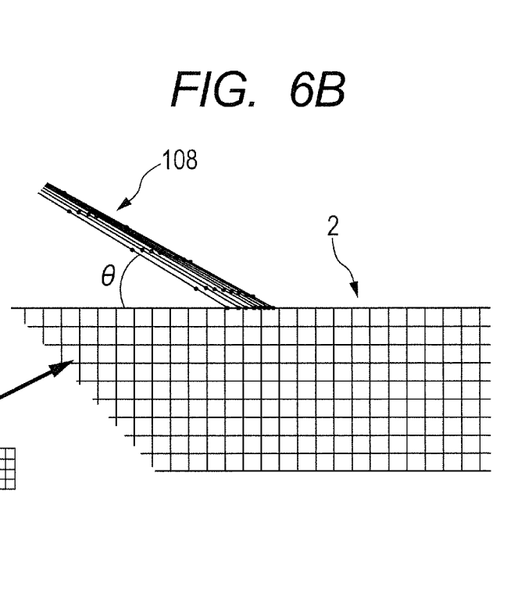
FIG. 6B is an enlarged view of the calculation result of the ion trajectory in the vicinity of the surface of a sample, according to the third exemplary embodiment of the present invention.

A third exemplary embodiment according to the present invention will be described below with reference to FIG. 6A and FIG. 6B which illustrate a part of a primary ion irradiation unit and a simulation result of an ion trajectory. FIG. 6B is an enlarged view in the vicinity of a portion in which a sample 2 is irradiated with the primary ion beam, in FIG. 6A.

The present exemplary embodiment is different from Exemplary Embodiment 1 in the arrangement of the ion irradiation unit 1 and the sample 2, the setting of the parameters and the beam trajectory. The structures which are common with those of the above described Exemplary Embodiment 1 are denoted by the same reference numerals, and the descriptions are omitted.

In the present exemplary embodiment, energy of the ion emitted from the primary ion generation section was set at 4 keV. In the ion deflection section, R1 was set at 60 mm, R2 was set at 40 mm, LR was set at 20 mm, and φ was set at 45 [deg]. The potential Vs of the surface of the sample was set at 0 V. The voltages of Vg1 and Vg2 applied to the electrodes of the ion deflection section were set at 1,250 V and −2,500 V, respectively. In addition, the incident angle θ of the beam on the surface of the sample was set at approximately 30 [deg]. A spread d of the beam when the beam was incident on the surface was set at approximately 2.5 mm.

In the present exemplary embodiment, the trajectories of the primary ions are once converged and then diverged again. However, as is understood also from FIG. 6B, each primary ion reaches the surface of the sample almost at the same time. Specifically, the dispersion in the path lengths of the primary ions was 0.7 mm at a maximum. Consequently, in the case of a Bi ion, the times at which the primary ions reach the surface of the sample are converged into 12 nsec or shorter.

As described above, the present exemplary embodiment also can suppress the dispersion in the times at which the primary ions reach the surface of the sample, when the primary ion beam having a spread has obliquely irradiated the surface of the sample. In addition, the present exemplary embodiment enables the primary ion source to be provided in a position separated from a secondary ion detecting device, and thereby enhances the flexibility of a structure of an apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-251552, filed Nov. 17, 2011, which is hereby incorporated by reference herein in its entirety.

The invention claimed is:

1. A mass distribution spectrometry method including irradiating a sample with a primary ion beam and detecting a generated secondary ion,
wherein the primary ion beam having a spread toward a direction perpendicular to a travelling direction is obliquely incident on a surface of the sample after a path length of each primary ion contained in the primary ion beam is adjusted by deflecting a trajectory between a primary ion source and the surface of the sample,
wherein the mass distribution spectrometry method is a projection type mass distribution spectrometry method, and
wherein path lengths of primary ions incident on arbitrary two points on the surface of the sample on which the primary ions are incident are adjusted so that:
a difference of the path lengths of the primary ions incident on the two points becomes smaller than d*cos θ, when d is defined as a distance in an incident direction of the ion beam between the arbitrary two points which have been projected on a horizontal plane on the surface of the sample, and θ is defined as an incident angle of an ion which is incident on either one of the points out of the two points.

2. The mass distribution spectrometry method according to claim 1, wherein the secondary ion is detected with a time-of-flight ion detection method.

3. The mass distribution spectrometry method according to claim 1, further comprising simultaneously detecting two-dimensionally positional information of secondary ions at a time when the secondary ions are generated.

4. The mass distribution spectrometry method according to claim 1, wherein the trajectory is deflected by an electrostatic force or a magnetic force.

5. The mass distribution spectrometry method according to claim 1, wherein the trajectory is deflected by an electrostatic force generated by a pair of deflection electrodes positioned so as to oppose each other with the trajectory sandwiched therebetween.

6. The mass distribution spectrometry method according to claim 1, wherein the arbitrary two points are two points of which the d becomes a maximal value of the distance in the incident direction of the ion beam between two points which the ions reach.

7. The mass distribution spectrometry method according to claim 1, wherein the generated secondary ion is projected to a two-dimensional ion detector.

8. The mass distribution spectrometry method according to claim 7, wherein the two-dimensional ion detector comprises a microchannel plate (MCP), a fluorescent plate, or a two-dimensional photodetector.

9. The mass distribution spectrometry method according to claim 1, wherein the path length is adjusted so that amounts of time for the primary ions to reach the surface of the sample become equal.

10. A mass distribution spectrometer including a primary ion irradiation unit and a detecting device for a secondary ion which has been generated by irradiation for a sample with a primary ion,
wherein the primary ion irradiation unit is configured to:
form a primary ion beam which has a spread toward a direction perpendicular to a travelling direction;
adjust a path length of each primary ion contained in the primary ion beam between a primary ion source and a surface of the sample, by deflecting a trajectory of the primary ion, so that a difference of path lengths of primary ions incident on two arbitrary two points on the surface of the sample becomes smaller than d*cos θ, when d is defined as a distance in an incident direction of the ion beam between the arbitrary two points which have been projected on a horizontal plane on the surface of the sample, and θ is defined as an incident angle of an ion which is incident on either one of the points out of the two points; and
irradiate the surface of the sample obliquely with the primary ion having the spread toward the direction perpendicular to the travelling direction, after the path length has been adjusted, and
wherein the mass distribution spectrometer is configured to perform projection type mass distribution spectrometry.

11. The mass distribution spectrometer according to claim 10, which comprises a two-dimensional ion detector for projecting the generated secondary ion.

12. The mass distribution spectrometer according to claim 11, wherein the two-dimensional ion detector comprises a microchannel plate (MCP), a fluorescent plate, or a two-dimensional photodetector.

13. A mass distribution spectrometer including a primary ion irradiation unit for irradiating a surface of a sample obliquely with a primary ion, and a detecting device for detecting a secondary ion which has been generated from the sample,
- wherein the primary ion irradiation unit has a deflection unit for deflecting paths of emitted primary ions toward an incident direction so that the emitted primary ions maintain a state having a spread toward a direction perpendicular to a travelling direction, so that amounts of time for the emitted primary ions to reach the surface of the sample become equal, and so that trajectories of the emitted primary ions are adjusted such that path lengths of all of the emitted primary ions become equal, and
- wherein the mass distribution spectrometer is configured to perform projection type mass distribution spectrometry.

14. The mass distribution spectrometer according to claim 13, further comprising:
- an acquiring unit for acquiring mass distribution on the surface of the sample from signals of the secondary ions, which have been detected by the detecting device; and
- a displaying unit for outputting the acquired mass distribution.

15. The mass distribution spectrometer according to claim 13, which comprises a two-dimensional ion detector for projecting the generated secondary ion.

16. The mass distribution spectrometer according to claim 15, wherein the two-dimensional ion detector comprises a microchannel plate (MCP), a fluorescent plate, or a two-dimensional photodetector.

17. A mass distribution spectrometry method including irradiating a sample with a primary ion beam and detecting a generated secondary ion,
- wherein the primary ion beam having a spread toward a direction perpendicular to a travelling direction is obliquely incident on a surface of the sample after a path length of each primary ion contained in the primary ion beam is adjusted by deflecting a trajectory between a primary ion source and the surface of the sample,
- wherein the mass distribution spectrometry method is a projection type mass distribution spectrometry method, and
- wherein the primary ion beam is incident on the surface of the sample, after the path length is adjusted between the primary ion source and the surface of the sample, so that amounts of time for primary ions to reach the surface of the sample become equal and path lengths of all of the primary ions become equal.

* * * * *